(12) United States Patent
Hafner et al.

(10) Patent No.: US 9,249,108 B2
(45) Date of Patent: Feb. 2, 2016

(54) MULTICOMPONENT SYSTEM OF ROSUVASTATIN CALCIUM SALT AND SORBITOL

(75) Inventors: Andreas Hafner, Gelterkinden (CH); Fritz Blatter, Reinach (CH); Martin Szelagiewicz, Basel (CH); Bernd Siebenhaar, Kandern-Wollbach (DE)

(73) Assignee: BASF SE, Ludwigshafen (DE)

( * ) Notice: Subject to any disclaimer, the term of this patent is extended or adjusted under 35 U.S.C. 154(b) by 423 days.

(21) Appl. No.: 13/574,005

(22) PCT Filed: Nov. 21, 2011

(86) PCT No.: PCT/EP2011/070520
§ 371 (c)(1),
(2), (4) Date: May 28, 2013

(87) PCT Pub. No.: WO2012/069394
PCT Pub. Date: May 31, 2012

(65) Prior Publication Data
US 2013/0237553 A1 Sep. 12, 2013

Related U.S. Application Data

(60) Provisional application No. 61/415,879, filed on Nov. 22, 2010.

(30) Foreign Application Priority Data

Nov. 22, 2010 (EP) .................................... 10192045

(51) Int. Cl.
C07D 239/42 (2006.01)
C07C 29/00 (2006.01)
C07C 31/26 (2006.01)
A61K 31/505 (2006.01)
A61K 47/26 (2006.01)
A61K 47/48 (2006.01)

(52) U.S. Cl.
CPC .............. *C07D 239/42* (2013.01); *C07C 29/00* (2013.01); *C07C 31/26* (2013.01); *A61K 31/505* (2013.01); *A61K 47/26* (2013.01); *A61K 47/4893* (2013.01)

(58) Field of Classification Search
None
See application file for complete search history.

(56) References Cited

U.S. PATENT DOCUMENTS

2008/0176878 A1 7/2008 Wizel et al.
2010/0069635 A1 3/2010 Bollikonda

FOREIGN PATENT DOCUMENTS

WO 00/42024 A1 7/2000
WO 2005/023779 A1 3/2005

(Continued)

OTHER PUBLICATIONS

U.S. Appl. No. 14/406,264, filed Dec. 8, 2014, Chiodo, et al.
U.S. Appl. No. 14/406,339, filed Dec. 8, 2014, Chiodo, et al.

(Continued)

*Primary Examiner* — Bethany Barham
*Assistant Examiner* — Barbara Frazier
(74) *Attorney, Agent, or Firm* — Oblon, McClelland, Maier & Neustadt, L.L.P

(57) ABSTRACT

A novel solid form of Rosuvastatin comprises as the active ingredient a salt of bis[(E)-7-[4-(4-fluorophenyl)-6-isopropyl-2-[methyl(methylsulfonyl)-amino]pyrimidin-5-yl]-(3R,5S)-3,5-dihydroxyhept-6-enoic acid] and sorbitol. The crystal comprising the two components, and minor amounts of water, shows improved properties such as crystallization behavior and stability.

12 Claims, 1 Drawing Sheet

(56) References Cited

FOREIGN PATENT DOCUMENTS

| WO | 2006/079611 | A1 | 8/2006 |
| WO | 2008/067440 | A2 | 6/2008 |

OTHER PUBLICATIONS

U.S. Appl. No. 14/234,158, filed Jan. 22, 2014, Hafner, et al.
U.S. Appl. No. 14/415,875, filed Jan. 20, 2015, Hafner, et al.
U.S. Appl. No. 14/433,147, filed Apr. 2, 2015, Chiodo, et al.
U.S. Appl. No. 14/360,799, filed May 27, 2014, Hafner, et al.

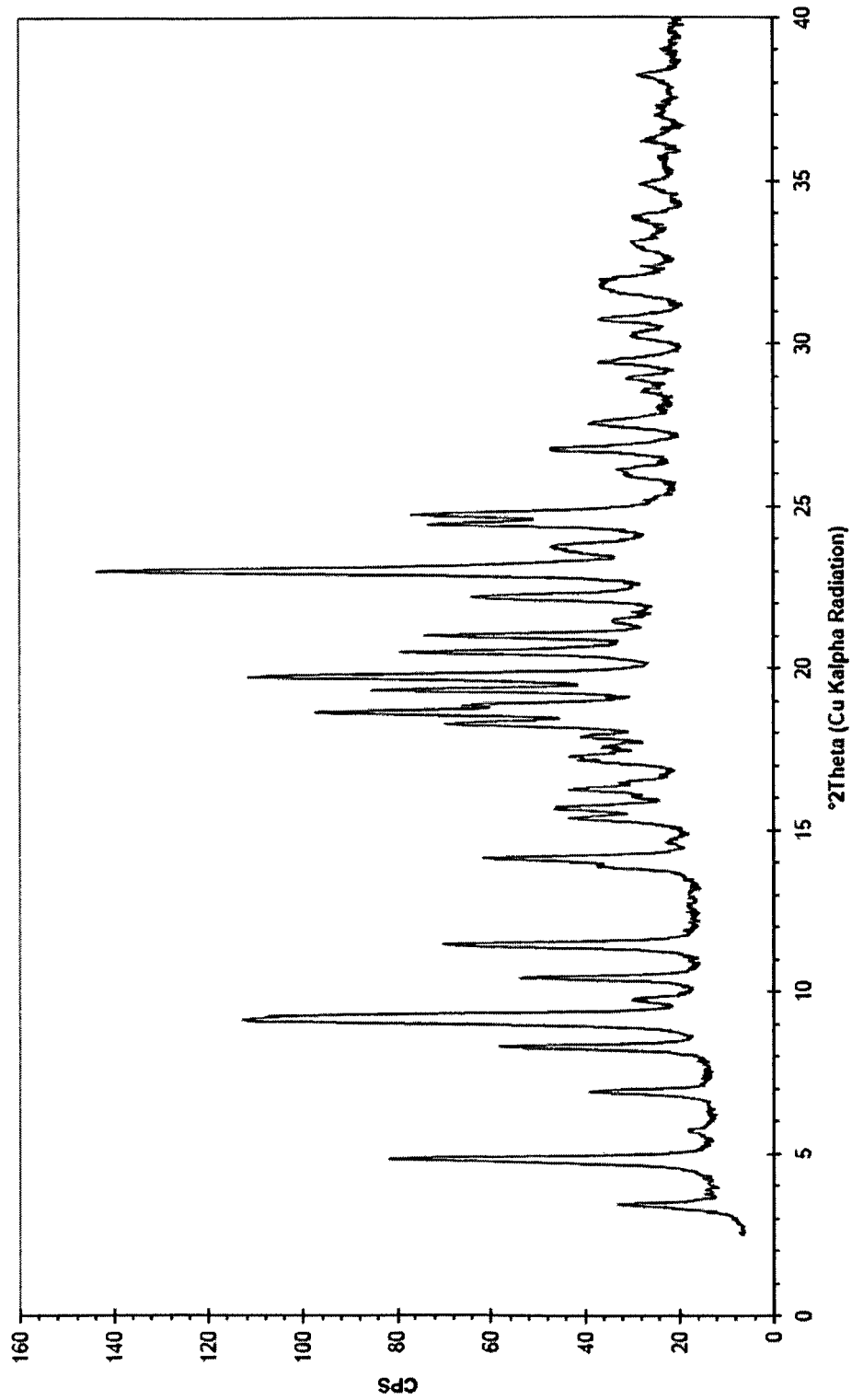

MULTICOMPONENT SYSTEM OF ROSUVASTATIN CALCIUM SALT AND SORBITOL

The present invention relates to a multicomponent system comprising rosuvastatin calcium salt and sorbitol, to pharmaceutical preparations comprising said system, and specifically to a homogenous crystalline phase (cocrystal) comprising rosuvastatin calcium and sorbitol. The invention also relates to processes for preparing said multicomponent system and crystalline phase. The invention also relates to compositions comprising said multicomponent system or crystalline phase and a pharmaceutically acceptable carrier, and to methods of using said multicomponent system or crystalline phase to treat a disease condition wherein inhibition of HMG CoA reductase is beneficial.

Rosuvastatin calcium is known as the calcium salt of bis [(E)-7-[4-(4-fluorophenyl)-6-isopropyl-2-[methyl(methylsulfonyl)amino]pyrimidin-5-yl](3R,5S)-3,5-dihydroxyhept-6-enoic acid], specifically the calcium salt of formula (1)

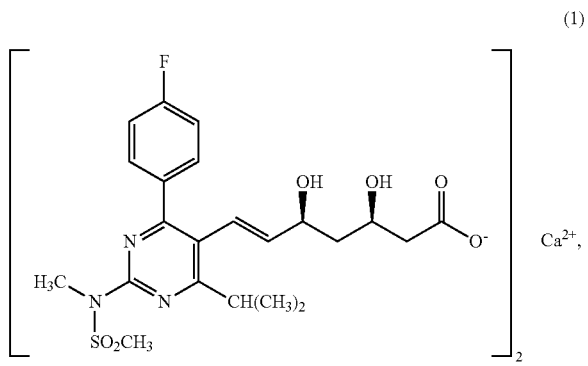

It is known to inhibit the HMG-CoA reductase, and subsequently suppress the biosynthesis of cholesterol. The compound is also known as Rosuvastatin hemicalcium salt, corresponding to half of the molecular weight shown in the above formula (1). Rosuvastatin calcium is useful in the treatment of hypercholesterolemia, hyperlipoproteinemia, and atherosclerosis. Rosuvastatin calcium may form hydrates with a varying content of water.

In WO 00/42024 is disclosed a crystalline form, hereafter referred to as form A of bis[(E)-7-[4-(4-fluorophenyl)-6-isopropyl-2-[methyl(methylsulfonyl)amino]pyrimidin-5-yl] (3R,5S)-3,5-dihydroxyhept-6-enoic acid] calcium salt and hydrates thereof, which are prepared by dissolving the amorphous form in a mixture of water and an organic solvent such as acetone or acetonitrile under heating and then cooling the solution to precipitate crystalline form A.

WO 06/079611 discloses some further crystalline forms of rosuvastatin calcium including form B. Further documents disclosing certain crystalline forms of rosuvastatin calcium are EP-A-1663989 and US-A-2008-176878. WO 08/067,440 discloses a salt of rosuvastatin with dehydroabietylamine.

Existing solid forms of rosuvastatin calcium still leave room for improvement of physical as well as biological characteristics. There exists a need for other solid forms, especially crystalline forms, of bis[(E)-7-[4-(4-fluorophenyl)-6-isopropyl-2-[methyl(methylsulfonyl)amino]pyrimidin-5-yl] (3R,5S)-3,5-dihydroxyhept-6-enoic acid] calcium salt for sufficient diversity on crystalline materials to optimize manufacture, formulation and biological efficiency.

SUMMARY OF THE INVENTION

The invention provides a novel solid form of rosuvastatin calcium characterized by a content of sorbitol and, consequently, novel pharmaceutical formulations containing this form. The invention further provides a novel crystalline form of rosuvastatin calcium, and processes for manufacture thereof.

Crystalline forms often show desired different physical and/or biological characteristics which may assist in the manufacture or formulation of the active compound, to the purity levels and uniformity required for regulatory approval. The present solid form, especially crystalline form, may possess improved pharmacological characteristics, for example, improved bioavailability, thus offering enhanced possibilities to modulate and design improved drug products.

DETAILED DESCRIPTION OF THE INVENTION

The solid form of the invention is a composite comprising two components, which are a rosuvastatin salt, especially rosuvastatin calcium, and sorbitol, especially D-sorbitol

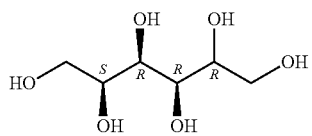

within one single phase. More specifically, the invention provides a multicomponent molecular crystal (i.e. a co-crystal) containing a salt of Rosuvastatin and sorbitol, preferably the hemi Ca salt of bis[(E)-7-[4-(4-fluorophenyl)-6-isopropyl-2-[methyl(methylsulfonyl)-amino]pyrimidin-5-yl](3R,5S)-3, 5-dihydroxyhept-6-enoic acid] and D-sorbitol.

The solid phase generally contains 0.3 to 1.5 molar parts, preferably 0.3 to 1.1 molar parts, of D-Sorbitol on 1 molar unit bis[(E)-7-[4-(4-fluorophenyl)-6-isopropyl-2-[methyl (methylsulfonyl)-amino]pyrimidin-5-yl](3R,5S)-3,5-dihydroxyhept-6-enoic acid]. The salt is preferably the calcium or sodium salt, especially the hemi calcium salt. Also possible are ratios of about 0.8 to about 1.2 mol sorbitol per mole of rosuvastatin hemicalcium salt, or about 0.4 to about 0.7 mol sorbitol per mole of rosuvastatin hemicalcium salt. Further examples are molar compositions sorbitol:rosuvastatin of about 1:1 (i.e. the 1:1 adduct), or of about 0.5:1 (i.e. 1:2 adduct).

The invention thus includes i) a multicomponent molecular crystal containing a salt of bis[(E)-7-[4-(4-fluorophenyl)-6-isopropyl-2-[methyl(methylsulfonyl)-amino]pyrimidin-5-yl](3R,5S)-3,5-dihydroxyhept-6-enoic acid] and Sorbitol;

ii) a multicomponent molecular crystal containing a hemi Ca salt of bis[(E)-7-[4-(4-fluorophenyl)-6-isopropyl-2-[methyl(methylsulfonyl)-amino]pyrimidin-5-yl](3R,5S)-3,5-dihydroxyhept-6-enoic acid] and D-Sorbitol;

iii) a multicomponent molecular crystal containing 0.3 to 1.5 molar parts, preferably 0.5 to 1.1 molar parts, and much preferred 0.9 to 1.1 molar parts, of D-Sorbitol on 1 molar part of bis[(E)-7-[4-(4-fluorophenyl)-6-isopropyl-2-[methyl(methylsulfonyl)-amino]pyrimidin-5-yl](3R,5S)-3,5-dihydroxyhept-6-enoic acid] as calcium and preferably as hemi calcium salt;

iv) a solid form as defined under i-iii consisting essentially of bis[(E)-7-[4-(4-fluorophenyl)-6-isopropyl-2-[methyl(methylsulfonyl)-amino]pyrimidin-5-yl](3R,5S)-3,5-dihydroxyhept-6-enoic acid] calcium salt, D-sorbitol, and water as minor component by weight.

Preferred solid form may be further characterized by its high crystallinity and/or high melting point of above 110° C. (m.p. e.g. from the range 110-128° C., especially from the range 115-122° C.) and high melting enthalpy (see present examples). While showing a solubility as good as solid forms of Rosuvastatin calcium previously known, the present solid form provides better stability, and provides advantages in processing due to its good crystallization properties.

Sorbitol and rosuvastatin are present in the same solid phase, preferably in the same crystalline phase, i.e. forming a co-crystal; hereinafter designated as form D. The invention thus further pertains to a novel crystalline form of rosuvastatin calcium, which crystalline form is characterized by containing sorbitol within its crystalline structure, e.g. in amounts as indicated above. A preferred novel crystalline form generally exhibits a characteristic X-ray powder diffraction pattern with characteristic peaks expressed in d-values (Å): 4.85 (s), 4.75 (s), 4.70 (s), 4.59 (s), 4.49 (vs), 4.33 (s), 4.23 (s), 4.00 (s), 3.86 (vs), 3.75 (s), 3.64 (s), 3.60 (s), 3.33 (s), 3.24 (s), 3.04 (s), 2.91 (s), 2.82 (s).

More specifically, the present invention comprises a crystalline form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof, which exhibits a characteristic X-ray powder diffraction pattern with characteristic peaks expressed in d-values (Å) as shown in the below table:

| d value [Angstroem] | Intensity |
|---|---|
| 25.36 | w |
| 18.09 | s |
| 12.73 | m |
| 10.62 | m |
| 9.62 | s |
| 8.45 | m |
| 7.70 | s |
| 6.26 | s |
| 5.65 | s |
| 5.44 | m |
| 5.14 | m |
| 4.95 | m |
| 4.85 | s |
| 4.75 | s |
| 4.70 | s |
| 4.59 | s |
| 4.49 | vs |
| 4.33 | s |
| 4.23 | s |
| 4.00 | s |
| 3.86 | vs |
| 3.75 | s |
| 3.64 | s |
| 3.60 | s |
| 3.43 | m |
| 3.33 | s |
| 3.24 | s |
| 3.09 | m |
| 3.04 | s |
| 2.96 | m |
| 2.91 | s |
| 2.82 | s |
| 2.72 | m |
| 2.57 | m | hereinafter designated as form D.

Here and in the following the abbreviations in brackets mean: (vs)=very strong intensity; (s)=strong intensity; (m)=medium intensity; (w)=weak intensity.

In still another preferred embodiment, the present invention comprises a crystalline form D of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof, which exhibits characteristic X-ray powder diffraction patterns as exhibited in FIG. 1.

Another object of the invention is a process for the preparation of crystalline form D of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt (Rosuvastatin calcium) and hydrates thereof which comprises the steps of a) providing sorbitol (especially D-sorbitol),
b) providing a solution of Rosuvastatin calcium (e.g. crude Rosuvastatin calcium or another form of Rosuvastatin in combination with an equivalent or excess amount of calcium, e.g. from synthesis) in a suitable solvent,
c) combining the solutions provided in steps (a) and (b), and
d) separating the precipitate and drying.

Step (a) usually comprises providing sorbitol in solid form, or as a solution of D-sorbitol in water, or water containing minor amounts of a water miscible solvent as defined for (b) below.

The solvent used in step (b) is water or a water miscible organic solvent such as an alcohol (e.g. methanol, ethanol, propanol, butanol), or an ester (such as ethyl acetate, methyl acetate), ethers such as methyl-tert.butylether, or an aliphatic ketone (e.g. acetone, methyl ethyl ketone), or mixture of such solvents, or such a solvent with water. Solutions according to steps (a) and (b) preferably are concentrated solutions.

The concentration of rosuvastatin calcium may range from 0.1 to about 300 mg/ml of solvents (including water), preferably from 20 to 200 mg/ml.

The process is preferably carried out in the temperature range 15-50° C., for example at ambient temperature. In a preferred process, step (c) is carried out at a temperature from the range 30-60° C. or the mixture is heated to a temperature from said range, e.g. about 50° C., especially in case that solid sorbitol is provided in step (a), with forming a solution. The solution thus tempered is then preferably cooled before step (d). In a preferred process, the cooling step is accompanied by seeding with crystals of form D (e.g. 1-10% b.w. of the total amount of rosuvastatin) at a temperature of about 25-30° C.

Ambient temperature means in the context of the invention a temperature range at room temperature, comprising 20 to 30° C. and preferably about 23 to 26° C.

Crystal form D is isolated by filtering off the crystals and drying, e.g. in vacuum, an inert gas flow or both at ambient temperature, or elevated temperatures up to 80° C.

Form D is thermodynamically stable and can be dried at elevated temperatures, e.g. below 80° C., and is obtained as a fine powder with typical particle size distributions with the median size between 1 and 50 μm, preferably between 1 to 10 p.m. This particle size range ensures a fast dissolution profile, while retaining the favourable handling properties in the formulation process.

Form D is less prone to water uptake under humidity, and is easy to formulate. Present Form D generally contains minor amounts of water, mainly within its crystal structure, the amounts usually ranging from 1.5 to 5% of water, relative to the total weight of the solid phase, especially of the crystalline form D.

The solid form D may be used in pharmaceutical compositions in the same way as other forms of Rosuvastatin calcium previously known. Additionally, present form D based on any pharmaceutically acceptable salt of rosuvastatin, such as sodium or calcium salt, may be employed as an intermediate or starting material to produce the pure active ingredient, e.g. in form of crystal form A.

The present invention is also directed to a pharmaceutical composition comprising a solid form containing sorbitol, or especially crystal form D, of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof, and a pharmaceutically acceptable carrier or diluent.

The amount of solid (especially crystalline) forms of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof substantially depends on type of formulation and desired dosages during administration time periods. The amount in an oral formulation may be from 0.1 to 200 mg, preferably from 0.5 to 100 mg, and more preferably from 1 to 50 mg.

Oral formulations may be solid formulations such as capsules, tablets, pills and troches, or liquid formulations such as aqueous suspensions, elixirs and syrups. Solid and liquid formulations encompass also incorporation of the present solid form, especially crystal form D, into liquid or solid food.

The solid forms according to the invention may be directly used as powders (micronized particles), granules, suspensions or solutions, or they may be combined together with other pharmaceutically acceptable ingredients in admixing the components and optionally finely divide them, and then filling capsules, composed for example from hard or soft gelatine, compressing tablets, pills or troches, or suspend or dissolve them in carriers for suspensions, elixirs and syrups. Coatings may be applied after compression to form pills.

Pharmaceutically acceptable ingredients are well known for the various types of formulation and may be for example binders such as natural or synthetic polymers, excipients, lubricants, surfactants, sweetening and flavouring agents, coating materials, preservatives, dyes, thickeners, adjuvants, antimicrobial agents and carriers for the various formulation types.

Examples for binders are gum tragacanth, acacia, starch, gelatine, and biological degradable polymers such as homo- or co-polyesters of dicarboxylic acids, alkylene glycols, polyalkylene glycols and/or aliphatic hydroxylcarboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, und natural polymers like chitosan, carragenan or hyaluronic aid.

Examples for excipients are phosphates such as dicalcium phosphate.

Examples for lubricants are natural or synthetic oils, fats, waxes, or fatty acid salts like magnesium stearate.

Surfactants may be anionic, anionic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartam.

Examples for flavouring agents are peppermint, oil of wintergreen or fruit flavours like cherry or orange flavour.

Examples for coating materials gelatine, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for liquid carriers are water, alcohols such as ethanol, glycerol, propylene glycol, liquid polyethylene glycols, triacetin and oils. Examples for solid carriers are talc, clay, microcrystalline cellulose, silica, alumina and the like.

The formulation according to the invention may also contain isotonic agents, such as sugars, buffers or sodium chloride.

The solid forms according to the invention may also be formulated as effervescent tablet or powder, which disintegrate in an aqueous environment to provide a drinking solution.

A syrup or elixir may contain the polymorph of the invention, sucrose or fructose as sweetening agent a preservative like methylparaben, a dye and a flavouring agent.

The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of Rosuvastatin calcium whereupon the properties that distinguish the solid forms of Rosuvastatin calcium are lost. However, the use of the novel forms to prepare such solutions is considered to be within the contemplation of the invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents.

A coated tablet may have a coating on the surface of the tablet or may be a tablet comprising a powder or granules with an enteric-coating.

Slow release formulations may also be prepared from the crystal form according to the invention in order to achieve a controlled release of the active agent in contact with the body fluids in the gastro intestinal tract, and to provide a substantial constant and effective level of the active agent in the blood plasma. The crystal forms may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The crystal forms of the invention are also useful for administering a combination of therapeutic effective agents to an animal. Such a combination therapy can be carried out in using at least one further therapeutic agent which can be additionally dispersed or dissolved in a formulation.

The crystal forms of this invention and its formulations respectively can be also administered in combination with other therapeutic agents that are effective to treat a given condition to provide a combination therapy.

The crystal forms and the pharmaceutical composition according to the invention are highly suitable for effective treatment of disorders in connection with need of inhibiting the HMG-CoA reductase, and subsequently suppressing the biosynthesis of cholesterol. Crystalline forms B and C of Rosuvastatin calcium and hydrates thereof and pharmaceutical composition are useful in the treatment of hypercholesterolemia, hyperlipoproteinemia, and atherosclerosis.

An object of the invention is also a therapeutic method for producing an HMG-CoA reductase inhibiting effect in a mammal comprising administering to a mammal in need of such therapy, an effective amount of the present composite containing sorbitol, especially crystal form D, of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt, and hydrates thereof.

The polymorphic forms of the invention may be used as single component or as mixtures with other solid forms, which may be crystalline or amorphous.

As to the novel polymorphic forms of Rosuvastatin calcium it is preferred that these contain 25-100% by weight, especially 50-100% by weight, of at least one of the novel forms, based on the total amount of Rosuvastatin calcium. Preferably, such an amount of the novel polymorphic forms of Rosuvastatin calcium is 75-100% by weight, especially 90-100% by weight. Highly preferred is an amount of 95-100% by weight.

Another object of the invention is a method of delivering a solid form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and/or hydrates thereof to a host, which method comprises administering to a host an effective amount of said solid form, especially crystal form D, according to the invention.

A further object of the invention is the use of a crystal form D and/or solid form containing sorbitol, of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt, and hydrates thereof, for the manufacture of a medicament useful in the treatment of disorders in connection with need of inhibiting the HMG-CoA reductase, and subsequently suppressing the biosynthesis of cholesterol, and especially useful in the treatment of hypercholesterolemia, hyperlipoproteinemia, and atherosclerosisin in a mammal, such as a human; and the solid forms according to the invention for use in medical therapy.

The following examples illustrate the invention.

Wherever noted, room temperature depicts a temperature from the range 18-23° C.; percentages are given by weight, if not indicated otherwise. Wherever mentioned in the examples, "sorbitol" stands for D-sorbitol.

ABBREVIATIONS

DMSO dimethyl sulfoxide
HPLC high pressure liquid chromatography
NMR nuclear magnetic resonance
FTIR Fourier-transformation infrared spectrometry
r.h. relative humidity (air, if not indicated otherwise)
TG thermogravimetry
v/v volume by volume Instrumental Powder X-ray diffraction: PXRD is carried out with a Bruker D8 Advance powder X-ray diffractometer using $Cu_{K-alpha}$ radiation in reflection (Bragg-Brentano) geometry. 2θ values are accurate within an error of ±0.1-0.2°. The samples are prepared without any special treatment other than the application of slight pressure to get a flat surface. About 3-5 mg of the sample are placed on a 0.1 mm depth standard silicon single crystal sample holder. The tube voltage is 40 kV and current was 40 mA. The PXRD diffractometer is equipped with a LynxEye detector. A variable divergence slight is used with a 3° window. The step size is 0.02° 2θ with a step time of 37 seconds. The samples are rotated at 0.5 rps during the measurement.

Thermogravimetry Coupled to Infrared Spectroscopy (TG-FTIR):

The thermo gravimetric measurements are carried out with a Netzsch Thermo-Microbalance TG 209 coupled to a Bruker FTIR Spectrometer IFS 28 or Vector 22 (sample pan with a pinhole, N2 atmosphere, heating rate 10 K/min, range 25° C. to 250° C.).

DSC:

Differential scanning calorimetry is carried out with a Perkin Elmer DSC7 using hermetically closed gold sample pans. Heating rate: 10K/minute.

1H-NMR:

The 1H-NMR spectra are recorded on a Bruker DPX 300 spectrometer.

Solvent: DMSO-d6.

Experimental

Solvents: For all experiments, Fluka or Merck grade solvents are used. Selected solvents are dried using 3 or 4 Å molecular sieves.

Crystallization Experiments:

The crystallization experiments are performed in Supelco amber glass vials using magnetic stirrers.

Aqueous Solubility Determination:

Approximately 0.5 mL of doubly distilled water is added to 16 to 39 mg of the substance to be measured. The resulting suspension is equilibrated in a temperature-controlled Eppendorf Thermomixer Comfort shaker for 2 h and 24 h at 25° C. at a shaking rate of 600 rpm. After 24 h the solid phase is recovered by filter centrifugation (0.10-µm PVDF membrane) and examined by XRPD. Concentrations in the filtrate after 2 h and 24 h (i.e., saturated solutions) are determined using HPLC. The pH of the saturated solution is determined with a Metrohm 713 pH meter.

EXAMPLE 1

Preparation of Cocrystal with Sorbitol (Form D)

Solution A: 182.1 mg of D-sorbitol are dissolved in 0.5 mL of water at room temperature.

Solution B: 502.9 mg of Rosuvastatin hemicalcium salt (amorphous form obtained from) are dissolved in 9.5 mL of acetone at room temperature.

Solution B is added to solution A over 10 minutes while stirring at room temperature (final acetone:water ratio 95:5 v/v; water activity approx. 0.57). The mixture is stirred at room temperature for 4 days. Several times over the 4 days, the mixture is sonicated. After 4 days the suspension is filtered and air dried for 10 minutes (23° C./39% r.h.). A small sample of the wet material is characterized by XRPD, which shows the pattern of crystal form D. The whole sample was then dried for 1 hour at approx. 50° C./30 mbar and stored at room temperature at 53% relative humidity for 3 days. The yield is approximately 69%. Characterization of the dried sample shows the pattern of crystal form D (see FIG. 1) and TG-FTIR shows a mass loss of 2.7% (water; 25° C. to 150° C.). 1H-NMR (measured in DMSO-d6) shows the spectrum of a mixture of Rosuvastatin and D-sorbitol (molar ratio Rosuvastatin:D-sorbitol approx. 1:0.9).

DSC (closed sample pan): Peak temperature: 120° C.; ΔH about 73 J/g (endothermal).

EXAMPLE 2

Preparation of Co-Crystal with Sorbitol (Form D)

503.1 mg of Rosuvastatin hemicalcium salt are dissolved in 10.0 mL of acetone+water 95:5 v/v (water activity approx. 0.57) at room temperature. 182.0 mg of D-sorbitol are added. The suspension is sonicated for 1 minute and stirred for 18 hours at room temperature. The suspension is seeded with approx. 10 mg of crystal form D (example 1), sonicated for 1 minute and stirred for 3 days at room temperature. Several times over the 3 days the mixture is sonicated. After 3 days an aliquot of the suspension (2.5 mL) is filtered and air dried for 10 minutes (26° C./41% r.h.). XRPD shows the pattern of crystal form D. The residual 7.5 mL of the suspension are also filtered, air dried for 10 minutes (26° C./41% r.h.) and dried for 1 hour at approx. 50° C./30 mbar. XRPD show the pattern of crystal form D. The total yield is approximately 73%. Characterization of the dried sample shows the pattern of crystal form D and TG-FTIR shows a mass loss of 2.8% (water; 25° C. to 150° C.). 1H-NMR (measured in DMSO-d6) shows the spectrum of a mixture of Rosuvastatin and D-sorbitol (molar ratio Rosuvastatin:D-sorbitol approx. 1:1).

EXAMPLE 3

Characterization of Co-Crystal

In order to further investigate the product obtained in examples 1 and 2, some additional experiments and characterizations are carried out:

(a) 1H-NMR measurements show that crystal form D contains D-sorbitol. The molar ratio of Rosuvastatin hemicalcium salt:D-sorbitol is approximately 1:1.
(b) The XRPD patterns do not indicate the presence of any of the five crystal forms of D-sorbitol given in publication Nezzal-2009 (Polymorphism of sorbitol, Journal of Crystal Growth 311, 2009, 3863-3870).
(c) The DSC diagram of example 1 measured in a closed DSC sample pan does not indicate the presence of any of the five crystal forms of D-sorbitol given in publication Nezzal-2009 (Polymorphism of sorbitol, Journal of Crystal Growth 311, 2009, 3863-3870) or the amorphous form. The melting peak does not indicate eutectic impurities. The melting temperature is well above the melting temperatures of the five known crystal forms of D-sorbitol.

Reference example (in accordance to Example 8 of U.S. Pat. No. 6,777,552): 451.1 mg of Rosuvastatin methylester (methyl(E)-7-[4-(4-fluorophenyl)-6-isopropyl-2-[methyl (methylsulfonyl)amino]pyrimidin-5-yl](3R,5S)-3,5-dihydroxy hept-6-enoate) is mixed with 10.0 mL of ethanol+water (1:1 v/v) at room temperature. Calcium hydroxyide (excess) and 24.5 mg of tetrabutyl ammonium bromide is added. The mixture is heated to a temperature of about 45° C. for about 3 hours. While the mixture is hot, filtration is done under vacuum to remove the excess calcium hydroxide. The mixture is then cooled to ambient temperature and stirred for about 20 minutes. The product is assessed by HPLC.

EXAMPLE 4

From the mixture obtained in the above reference example, Rosuvastatin calcium is precipitated by removing ethanol under reduced pressure and cooling to 3° C. The solid material is collected by filtration and dried. Subsequently, the material is processed in analogy to example 2 by dissolving in acetone+water 95:5 v/v, addition of D-sorbitol, sonication, stirring, seeding with crystal form D, isolation and drying. Purity of the product, as assessed by HPLC, is distinctly better than the material obtained in the reference example.

BRIEF DESCRIPTION OF FIGURES

FIG. 1: Powder X-Ray Diffraction pattern of Rosuvastatin hemicalcium salt/crystal form D (1:1 co-crystal with D-sorbitol)

The invention claimed is:
1. A single phase solid form of a bis[(E)-7-[4-(4-fluorophenyl)-6-isopropyl-2-[methyl(methylsulfonyl)-amino]pyrimidin-5-yl](3R,5S)-3,5-dihydroxyhept-6-enoic acid] salt comprising sorbitol, which is a co-crystal.
2. Solid form of claim 1 wherein the salt of bis[(E)-7-[4-(4-fluorophenyl)-6-isopropyl-2-[methyl(methylsulfonyl)-amino]pyrimidin-5-yl](3R,5S)-3,5-dihydroxyhept-6-enoic acid] is a calcium salt.
3. Solid form according to claim 1 wherein sorbitol is D-sorbitol.
4. Solid form according to claim 1 containing 0.3 to 1.5 molar parts, preferably 0.3 to 1.1 molar parts, of D-sorbitol on 1 molar unit of bis[(E)-7-[4-(4-fluorophenyl)-6-isopropyl-2-[methyl(methylsulfonyl)-amino]pyrimidin-5-yl](3R,5S)-3,5-dihydroxyhept-6-enoic acid].
5. Solid form according to claim 1, consisting essentially of bis[(E)-7-[4-(4-fluorophenyl)-6-isopropyl-2-[methyl(methylsulfonyl)-amino]pyrimidin-5-yl](3R,5S)-3,5-dihydroxyhept-6-enoic acid] calcium salt, D-sorbitol, and water as minor component by weight.
6. Solid form according to claim 1, which is a crystalline form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt with D-sorbitol, and/or hydrates thereof, exhibiting a X-ray powder diffraction pattern with characteristic peaks expressed in d-values (Å):

4.85 (s), 4.75 (s), 4.70 (s), 4.59 (s), 4.49 (vs), 4.33 (s), 4.23 (s), 4.00 (s), 3.86 (vs), 3.75 (s), 3.64 (s), 3.60 (s), 3.33 (s), 3.24 (s), 3.04 (s), 2.91 (s), 2.82 (s).

7. Solid form according to claim 1, which is a crystalline form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid]calcium salt with D-sorbitol, and/or hydrates thereof, which exhibits a characteristic X-ray powder diffraction pattern with characteristic peaks expressed in d-values (Å) as shown in the below table:

| d value [Angstroem] | Intensity |
|---|---|
| 25.4 | W |
| 18.1 | S |
| 12.7 | M |
| 10.6 | M |
| 9.6 | S |
| 8.5 | M |
| 7.7 | S |
| 6.3 | S |
| 5.65 | S |
| 5.44 | M |
| 5.14 | M |
| 4.95 | M |
| 4.85 | S |
| 4.75 | S |
| 4.70 | S |
| 4.59 | S |
| 4.49 | vs |
| 4.33 | S |
| 4.23 | S |
| 4.00 | S |
| 3.86 | vs |
| 3.75 | S |
| 3.64 | S |
| 3.60 | S |
| 3.43 | M |
| 3.33 | S |
| 3.24 | S |
| 3.09 | M |
| 3.04 | S |
| 2.96 | M |
| 2.91 | S |
| 2.82 | S |
| 2.72 | M |
| 2.57 | M. |

8. Solid form according to claim 1, comprising a crystalline form of bis[(E)-7-[4-(4-fluorophenyl)-6-isopropyl-2-[methyl(methylsulfonyl)amino]pyrimidin-5-yl]-(3R,5S)-3,5-dihydroxyhept-6-enoic acid] calcium salt with D-sorbitol, and/or hydrates thereof, which exhibits a characteristic X-ray powder diffraction pattern essentially as exhibited in FIG. 1.

9. Process for the preparation and/or purification of a solid form according to claim 1, which process comprises the steps of
   a) providing a solution of D-sorbitol in water,
   b) providing a solution of Rosuvastatin calcium in a suitable solvent,
   c) combining the solutions provided in steps (a) and (b), and
   d) separating the precipitate and drying.

10. Pharmaceutical composition comprising the solid form according to claim 1, and a pharmaceutically acceptable carrier or diluent.

11. A therapeutic method for producing an HMG-CoA reductase inhibiting effect in a mammal, which method comprises administering to a mammal in need of such therapy, an effective amount of a solid form according to claim 1.

12. A method of delivering a solid form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and/or hydrates thereof, which method comprises administering to a host an effective amount of a solid form according to claim 1.

* * * * *